United States Patent [19]
Kirchhevel

[11] Patent Number: 5,801,384
[45] Date of Patent: Sep. 1, 1998

[54] INFRARED GAS SPECTROMETER HAVING SEALED SECTIONS FOR IMPROVED SAFETY

[75] Inventor: G. Lamar Kirchhevel, Westminster, Colo.

[73] Assignee: Ohmeda Inc., Liberty Corner, N.J.

[21] Appl. No.: 921,429

[22] Filed: Aug. 29, 1997

[51] Int. Cl.$^6$ .................. G01N 21/01; G01N 21/35
[52] U.S. Cl. .................. 250/345; 250/343; 250/239; 340/605; 600/532
[58] Field of Search .................. 250/239, 339.02, 250/339.06, 339.13, 343, 345; 340/605, 606; 600/529, 532, 543, 310

[56] References Cited

U.S. PATENT DOCUMENTS

| | | | |
|---|---|---|---|
| 4,147,431 | 4/1979 | Mann | 250/458.1 |
| 4,982,089 | 1/1991 | Johnson | 250/343 |
| 5,510,612 | 4/1996 | Scofield et al. | 250/239 |

Primary Examiner—Edward J. Glick
Assistant Examiner—Darren M. Jiron
Attorney, Agent, or Firm—Roger M. Rathbun

[57] ABSTRACT

An infrared spectrometer for anesthetic gas monitoring using an infrared light source is divided into two separately sealed sections. A partition wall separating the two sections contains a partition window allowing infrared light to pass from the infrared source into a sealed sample chamber. In case of a failure of the sealed sample chamber the gas does not come into contact with the infrared source, thereby minimizing the risk of possible explosion. A gasket of neoprene or butyl rubber is used to seal the two sections from one another. The signal produced by the spectrometer indicating the composition of the sample gas is monitored to alert the user of a single point failure at the seal of the sample chamber.

13 Claims, 2 Drawing Sheets

5,801,384

INFRARED GAS SPECTROMETER HAVING SEALED SECTIONS FOR IMPROVED SAFETY

FIELD OF THE INVENTION

This invention relates to gas spectrometers for measuring the concentration of predefined components of a gas sample, particularly those spectrometers using an infrared source to transmit light through a sample gas containing a combination of possibly combustible gases such as oxygen, anesthetic gas agents and other gases found in a respiratory gas stream.

BACKGROUND OF THE INVENTION

Infrared gas spectrometers are utilized in a variety of industrial and medical applications to monitor the presence and concentration of one or more predefined components in a gas sample. Typically, light having a known spectral content is transmitted through a sample of the gas being analyzed and the transmitted light is detected at a number of different center wavelengths providing detected light intensities at these various center wavelengths. By processing the detected light intensities using known light absorption characteristics of the gas components under analysis, the concentrations of the individual gas components can be determined.

In infrared spectrometers the infrared light source is usually a resistive element with a surface temperature of 800° C. or higher. The sample gas in a respiratory gas monitor may contain a mixture of carbon dioxide and/or oxygen and one or more anesthetic agents such as nitrous oxide, halothane, enflurane, isoflurane, sevoflurane and/or desflurane. This mixture of gases is often combustible and can be ignited in the presence of the infrared light source. Thus, the infrared light source has typically been separated from the sample gas by a transparent window in the sample chamber. As will be appreciated, this provides only a single-point failure hazard, wherein the failure of one sample chamber window would allow the combustible gas mixture to leak into the area of the infrared spectrometer having the infrared source possibly resulting in ignition of the sample gas and explosion of the device.

SUMMARY OF THE INVENTION

In view of the foregoing, a primary object of the present invention is to provide a gas spectrometer having improved safety.

A related objective is to provide a gas spectrometer which is more durable and rugged and will continue operating in a safe manner.

A further objective is to provide the improved safety without reducing the effectiveness of the spectrometer by avoiding a significant reduction in the light transmitted from the infrared (IR) source to the sample gas chamber.

An even further object of this invention is to provide for the detection of a failure of the sample chamber in order to instruct the user to provide a new sample chamber.

To achieve such objectives and realize advantages, the gas spectrometer of the present invention is divided into two sealed sections: one section containing the infrared source and a second section containing the sample chamber. The two sections are separated by a partition wall containing a partition window which allows the light to pass from the IR source to the sample chamber, but prevents the sample gas from reaching the IR source.

An additional embodiment of the present invention provides for a spectrometer having a failure detection mode. In a respiratory gas monitor the path length of the sample cell has a fixed known length. Additionally the path lengths from the partition to the sample cell and from the sample cell to the detector are also known. If the sample gas were to leak from the sample cell into the sample cell side of the partition then the detector would be measuring the absorption of the transmitted light by the sample gas over a much longer path length equal to the sample cell path length plus the partition-to-sample-cell path length and the sample-cell-to-detector path length. Through the processing of the light intensities received by the detector an out-of-range condition can be detected and the user can be notified that a single point failure at the sample cell seal has occurred.

DETAILED DESCRIPTION OF THE DRAWINGS

Figure 1:
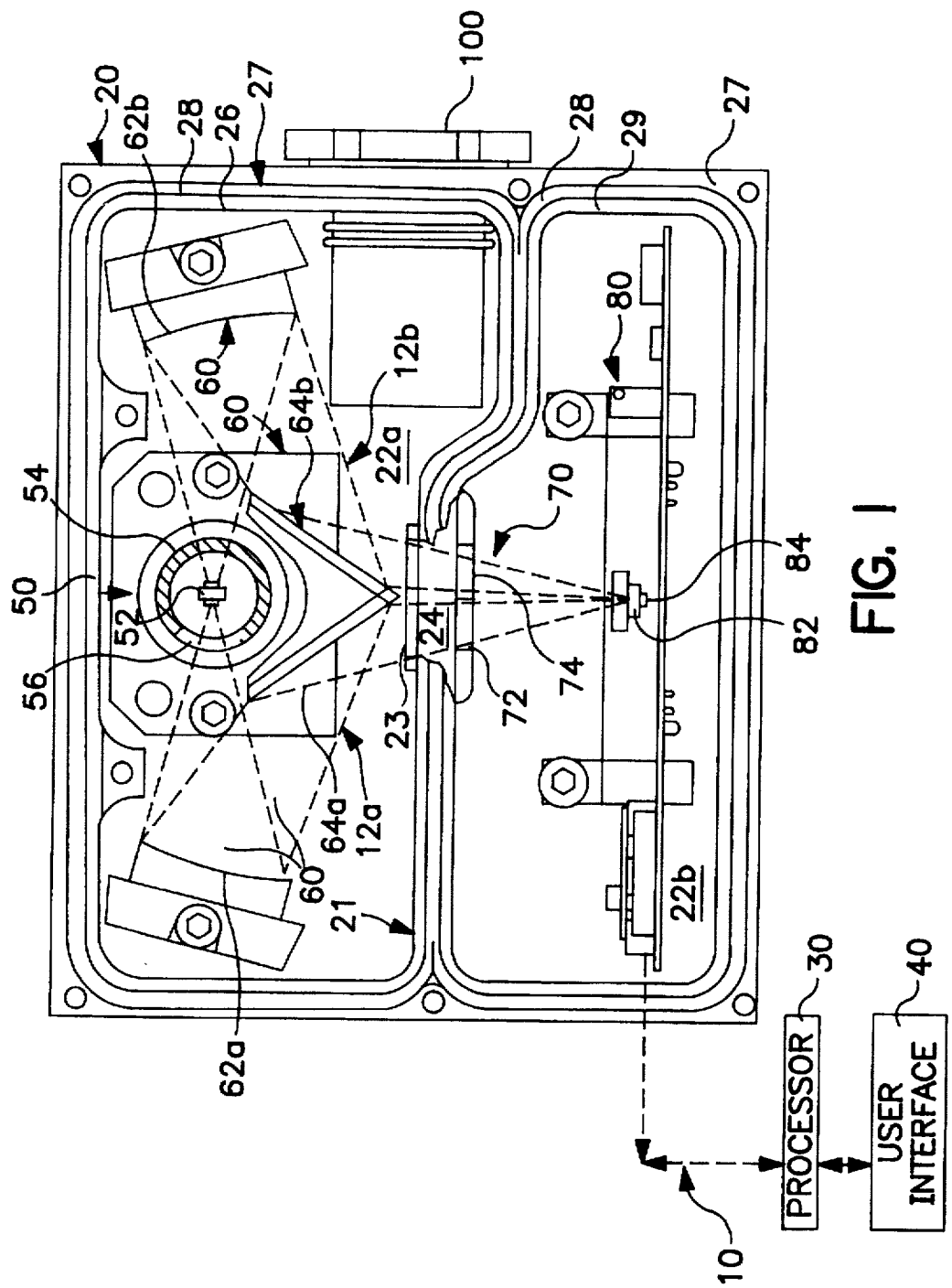
FIG. 1 is a top view of a housing assembly, shown in schematic combination with other components of a spectrographic respiratory gas monitor according to the present invention.

FIG. 1 illustrates an embodiment of the respiratory gas spectrometer 10 of the present invention, including a partially cut away view of a housing assembly 20 shown in schematic combination with a processor 30 and user interface 40. The housing assembly 20 defines an enclosed primary containment section 22a having an infrared radiation assembly 50, optical assembly 60 and gas component removal assembly 100 all at least partially disposed therein. The housing assembly 20 also defines an enclosed secondary containment section 22b having a detector assembly 80 and gas sampling assembly 70 disposed therein. These components cooperate to provide for the monitoring of the concentration of certain pre-selected components within respiratory gas stream samples which are cycled through the gas sampling assembly 70. In this regard, the present invention may be readily utilized in a respiratory gas spectrometer as disclosed in U.S. patent application No. 08/403,161, hereby incorporated by reference in its entirety.

The infrared radiation assembly 50 includes an elongated, upstanding infrared (IR) source element 52 and a cylindrical, concentrically disposed light chopper 54. Chopper 54 includes a window 56 and is rotatable about source element 52 for alternatingly transmitting radiation on first and second optical paths 12a and 12b, at least partially defined by optical assembly 60.

Optical assembly 60 includes first and second spherical mirrors 62a and 62b, for collecting and directing radiation from source element 52 on first and second optical paths 12a and 12b, respectively. The resultant and converging optical beams on paths 12a and 12b are separately redirected via first and second flat mirrors 64a and 64b, respectively.

As illustrated, the housing assembly 20 includes an internal partition wall 21 defining the separately sealed containment sections 22a and 22b. Internal partition wall 21 is provided with an opening 24 therethrough so as to receive gas sampling assembly 70 and transparent window member 23, as shown by the partially cut away portion of wall 21 in FIG. 1. Both window member 23 and gas sampling assembly 70 are positioned on optical paths 12a and 12b. The gas sampling assembly 70 includes a sample gas chamber 72 and reference gas chamber 74 disposed relative to optical assembly 60 such that the first converging beam on path 12a passes through opposing, transparent windows of sample gas chamber 72, and the second converging beam path 12b passes through opposing, transparent windows of the reference gas chamber 74. The gas sample assembly 70 is interconnected to gas flow lines (not shown) for continuously cycling a sample stream of respiratory gas from a patient through the sample gas chamber 72.

The detector assembly 80, includes a linear variable filter (not shown), an adjacent $CO_2$ band pass filter 82 positioned thereabove, and a linear array of pyro-electric detector elements 84 positioned behind the linear variable filter and band pass filter 82. The detector assembly 80 is positioned so that non-absorbed radiation transmitted through sample gas chamber 72 and reference gas chamber 74 on paths 12a and 12b, respectively, is filtered by linear variable filter and the band pass filter 82 and detected by linear detector array 84. As will be appreciated the detected radiation will not include radiation that is absorbed by gas components present along paths 12a and 12b, including, in particular gas components contained within sample gas chamber 72. In operation the linear variable filter will simultaneously filter transmitted radiation in a spatially distributed manner across a wavelength range, including the 7–10 micron range. The 7–10 micron range covers sub-ranges across which many anesthetic gas agents will display unique radiation absorbance characteristics. The $CO_2$ band pass filter 82 will pass unabsorbed radiation in the 4–5 micron range, which range encompasses that within which carbon dioxide displays unique radiation absorbance characteristics. By utilizing detector array 84 to simultaneously obtain intensity measurement values at predetermined center wavelengths across the 7–10 micron and 4–5 micron wavelength ranges, the resultant data can be provided to processor 30 for multivariate statistical processing and the determination of the concentration of one or more anesthetic gas agents and carbon dioxide for visual and/or audible output to the user via user interface 40.

As can be seen from the foregoing description of the gas spectrometer 10 for measurement of the concentration of various anesthetic gas agents and carbon dioxide, the continued separation of the sample gas from the IR source is of great importance in ensuring the safety of the device. Therefore, the configuration of the components of the device which assures continued separation will now be described in greater detail.

In FIG. 1 the primary containment section 22a and secondary containment section 22b are separated by internal partition wall 21 which is preferably an integral portion of the housing assembly 20 which is preferably a machined metal assembly but which also could be comprised of a molded or extruded plastic, such as polycarbonate. The perimeter of the primary containment section 22a is defined by an interior ridge portion 26, a depression 28 and an exterior ridge portion 27. Likewise the perimeter of the secondary containment section 22b is defined by an interior ridge portion 29, depression 28 and exterior ridge portion 27. The top 25 (shown only in FIG. 2) of housing assembly 20 is designed so as to have a ridge portion 31 (shown only in FIG. 2) which mates with depression 28. Furthermore a gasket having the shape of depression 28 is used to complete the gas impervious seal between primary containment section 22a and secondary containment section 22b. Top 25 could also be flat at the perimeter and a gasket which would fit into depression 28 would provide the necessary seal. The gasket 35 is preferably made of neoprene which has been found to be favorable due to its low carbon dioxide and water vapor permeability properties. Alternatively, any other gasket material which would be known to provide a seal against the passage of gases from one containment section to another and which would not be harmed by the gases which are to be encountered in the gas spectrometer could be used. In the case of an anesthetic gas monitor such materials would include materials such as butyl rubber.

Internal partition wall 21 includes a transparent window member 23 which is affixed over the opening 24 in internal partition wall 21 using a gas impervious adhesive in order to provide a barrier to the transmission of gas between primary containment section 22a and secondary containment section 22b.

Figure 2:
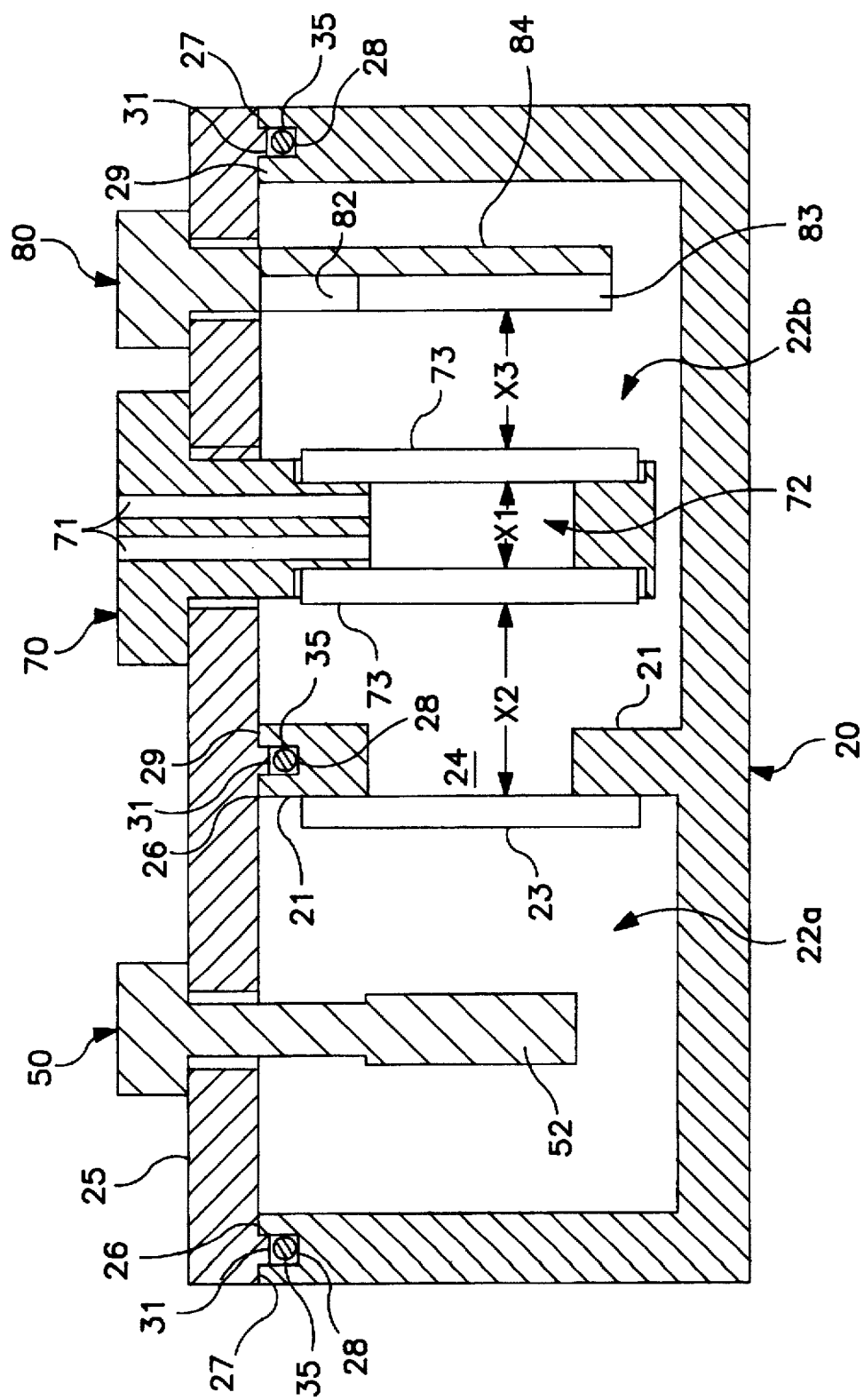
FIG. 2 is a simplified cross sectional side view of the housing assembly and other components of the spectrographic respiratory gas monitor according to the present invention.

FIG. 2 depicts in cross-section an embodiment of the present invention similar in many respects to that discussed above with regard to FIG. 1. Infrared radiation assembly 50 having an infrared source 52 is disposed in primary containment section 22a which is comprised of certain portions of housing assembly 20 and top 25. Gas sample assembly 70 having sample gas chamber 72 and a reference gas chamber (not shown in FIG. 2) partially enclosed by transparent sample chamber windows 73 along with detector assembly 80 having linear variable filter 83 and $CO_2$ band pass filter 82 in front of pyroelectric detector array 84 are disposed in secondary containment section 22b which is comprised of a certain portion of housing assembly 20 and top 25.

Housing assembly 20 has an internal partition wall 21 which has an opening 24 therethrough. The left-hand portion of housing assembly 20 has an exterior ridge 27, a depression 28 and an interior ridge 26, the latter two of which follow through to the internal partition wall 21. The right-hand portion of housing assembly 20 has the exterior ridge 27, depression 28 and interior ridge 29 the latter two of which follow through to the internal partition wall 21. Top 25 has a central ridge 31 which is designed to mate with depression 28 in the walls of the housing assembly 20. A gasket 35 is set into depression 28 in order to provide for a gas impervious seal between primary containment section 22a and secondary containment section 22b. The adhesive which adheres transparent window member 23 to the IR source side of internal partition wall 21 completes the sealing of the two containment sections from one another.

The sealed dual chamber design of the housing also enables safe detection of single point failures of the sample chamber window seal. Referring to FIG. 2, the sample cell path length is denoted as X1. Distance X2 denotes the path length between the transparent window member 24 and left sample chamber window 73. Distance X3 is the path length between the right sample chamber window 73 and the linear variable filter 83. All of these distances, X1, X2 and X3 are known. During normal operation infrared radiation passes from infrared source element 52 through sample gas chamber 72, and, alternatively, reference gas chamber 74, wherein certain wavelengths of radiation are absorbed and certain wavelengths pass through depending on the composition of the sample gas. The path length of the absorption is only X1 under normal conditions.

If sample gas chamber 72 begins to leak, then sample gas will be pumped into secondary containment section 22b. A certain amount of carbon dioxide, anesthetic agent or other gas will now exist in the secondary containment section 22b along optical paths X1, X2 and X3. The infrared radiation will now be absorbed by molecules of these leaked gases which exist along path lengths X1, X2 and X3 combined, thereby changing the signal measured by the detector array 84, i.e., indicating a higher absorbtion of infrared radiation than would have otherwise been measured without leakage from sample gas chamber 72. Thus, monitoring the changes in the measured irradiation or detected composition of the sample gas can alert the user to leakage of respiratory gas from the sample gas chamber 72, i.e., the detected composition of the gas will be so distorted as to be completely off the scale of possible gas concentrations.

It would also be possible to monitor the signal representing the composition and concentration of gas components in the reference gas. Changes in the absorbtion of infrared radiation along the reference light path 12b or the appearance of gases in the signal representing the reference gas which were not previously present, as well as the presence of additional quantities of gas components above initial threshold levels, would indicate leakage of gas from the sample gas chamber 72.

Upon recognition of a leak in the seal of sample gas chamber 72 processor 30 would display a warning such as "CHECK SAMPLE CHAMBER SEAL" to the user on user interface 40 or some other warning which would alert the user to the failure. This will enable corrective action to take place before a failure of the seal between the primary and secondary containment sections could result in an explosion.

It should be appreciated that the foregoing is a description of merely a few of the embodiments of the present invention and that there are many additional embodiments which would be apparent to those skilled in the art and which would be within the scope of the present invention as defined by the following claims.

What is claimed is:

1. A respiratory gas analyzer for determining the concentration of one or more predefined components of a respiratory gas sample, comprising:

a housing assembly defining a primary containment section and a secondary containment section wherein said primary containment section and said secondary containment section share a partition wall in said housing assembly;

an infrared radiation source positioned within said primary containment section of said housing assembly whereby said infrared radiation source generates a plurality of beams of infrared radiation;

a sample gas chamber having opposing transparent walls and being positioned within said secondary containment section of said housing assembly for receiving a respiratory gas sample;

a detector assembly positioned within said secondary containment section for receiving said plurality of beams of infrared radiation which pass through said transparent walls of said sample gas chamber and for generating a signal indicative of the concentration of said one or more predefined components of said respiratory gas sample;

a partition window in said partition wall for allowing the transmission of infrared radiation from said primary containment section to said secondary containment section; and, means for sealing said primary containment section from said secondary containment section so as to prevent said respiratory gas sample from entering said primary containment section in the event said respiratory gas sample leaks from said sample gas chamber.

2. A respiratory gas analyzer according to claim 1 wherein said housing assembly comprises:

a bottom portion having a bottom and four exterior walls and said partition wall; and, a top portion.

3. A respiratory gas analyzer according to claim 2 wherein said four exterior walls and said partition wall each have a depression at the end opposite the bottom.

4. A respiratory gas analyzer according to claim 3 wherein said top portion has a ridge around its perimeter adapted to removeably engage said depression in said bottom portion.

5. A respiratory gas analyzer according to claim 3 wherein said means for sealing comprises a gasket disposed in said depression of said bottom portion of said housing assembly.

6. A respiratory gas analyzer according to claim 5 wherein said gasket is comprised of neoprene.

7. A respiratory gas analyzer according to claim 5 wherein said gasket is comprised of butyl rubber.

8. A respiratory gas analyzer according to claim 1 further comprising an optical assembly positioned within said primary containment section for directing said plurality of beams of infrared radiation through said partition window and through said transparent walls of said sample gas chamber onto said detector assembly.

9. A respiratory gas analyzer according to claim 1 further comprising a means for monitoring said signal indicative of the concentration of said one or more predefined gas components in order to determine whether said respiratory gas is leaking from said sample gas chamber.

10. A method for detecting a failure of a sample gas chamber in a respiratory gas analyzer comprising the steps of:

generating a beam of infrared radiation from an infrared radiation source housed in a primary sealed section of a housing assembly;

transmitting said beam of infrared radiation through a respiratory gas sample contained in said sample gas chamber housed in a secondary sealed section of said housing assembly said primary sealed section and secondary sealed section having at least a partially transparent adjacent wall for communication of said beam from said primary sealed section to said secondary sealed section;

receiving said transmitted beam of infrared radiation on a detector array housed in said secondary sealed section;

generating a signal indicative of the concentration of one or more components of the respiratory gas sample;

monitoring said generated signal and comparing said signal to previously generated signals in order to determine if said respiratory gas sample is leaking from said sample chamber into said secondary sealed section of said housing assembly.

11. The method for detecting a failure of a sample gas chamber, according to claim 10 further comprising the steps of:

generating an alarm signal upon determining that said respiratory gas sample is leaking from said sample chamber into said secondary sealed section; and, displaying said alarm signal.

12. A method for detecting a failure of a sample gas chamber containing a respiratory gas sample in a respiratory gas analyzer comprising the steps of:

generating a beam of infrared radiation from an infrared radiation source housed in a primary sealed section of a housing assembly;

transmitting said beam of infrared radiation through a reference gas contained in a reference gas chamber housed in a secondary sealed section of said housing assembly said primary sealed section and secondary sealed section having at least a partially transparent adjacent wall for communication of said beam from said primary sealed section to said secondary sealed section;

receiving said transmitted beam of infrared radiation on a detector array;

generating a signal indicative of the concentration of one or more components of the reference gas sample;

comparing said signal with a predetermined threshold value for each of a plurality of gas components in order to determine if said respiratory gas sample is leaking from said sample chamber into said secondary sealed section of said housing assembly.

13. The method for detecting a failure of a sample gas chamber according to claim 12 further comprising the steps of:

generating an alarm signal upon determining that said respiratory gas sample is leaking from said sample chamber into said secondary sealed section; and, displaying said alarm signal.

* * * * *